US011446010B2

(12) United States Patent
Cahojova et al.

(10) Patent No.: US 11,446,010 B2
(45) Date of Patent: Sep. 20, 2022

(54) VAGINAL DEVICE AND METHOD FOR MEASURING FERTILITY-RELATED PARAMETER

(71) Applicants: Lady Technologies, Inc., San Francisco, CA (US); Kristina Cahojova, San Francisco, CA (US); Hynek Jamelik, Brno (CZ); Klara Erlebachova, Chroustov (CZ); Barbora Klembarova, Poprad (SK)

(72) Inventors: Kristina Cahojova, San Francisco, CA (US); Hynek Jemelik, Brno (SK); Klara Erlebachova, Chroustov (CZ); Barbora Klembarova, Poprad (SK)

(73) Assignee: Lady Technologies, Inc., San Francisco, CA (US)

( * ) Notice: Subject to any disclaimer, the term of this patent is extended or adjusted under 35 U.S.C. 154(b) by 170 days.

(21) Appl. No.: 16/491,926

(22) PCT Filed: Dec. 17, 2018

(86) PCT No.: PCT/US2018/066089
§ 371 (c)(1),
(2) Date: Sep. 6, 2019

(87) PCT Pub. No.: WO2019/118985
PCT Pub. Date: Jun. 20, 2019

(65) Prior Publication Data
US 2020/0297327 A1 Sep. 24, 2020

Related U.S. Application Data

(60) Provisional application No. 62/599,727, filed on Dec. 17, 2017.

(51) Int. Cl.
*A61B 5/00* (2006.01)
*A61B 10/00* (2006.01)
(Continued)

(52) U.S. Cl.
CPC .......... *A61B 10/0012* (2013.01); *A61B 5/002* (2013.01); *A61B 5/02055* (2013.01);
(Continued)

(58) Field of Classification Search
None
See application file for complete search history.

(56) References Cited

U.S. PATENT DOCUMENTS 5,209,238 A * 5/1993 Sundhar ............. A61B 10/0012
600/551
5,240,010 A * 8/1993 Weinmann ......... A61B 10/0012
600/551
(Continued)

OTHER PUBLICATIONS

Electronics Tutorials, MOSFET as a Switch, https://www.electronics-tutorials.ws/transistor/tran_7.html, viewed on Jul. 25, 2022.*
(Continued)

*Primary Examiner* — Lynsey C Eiseman
*Assistant Examiner* — James Moss
(74) *Attorney, Agent, or Firm* — J. Steven Svoboda

(57) ABSTRACT

A vaginal device configured to be inserted in a vagina of a user, the vaginal device comprising: a body comprising at least two electrodes configured to measure a fertility-related parameter of the user; a power source configured to provide power to the device; and an electrical system operably connected to the power source, the electrical system operably connected to one or more of the electrodes, the electrical system configured to switch one or more of the electrodes between charging and measuring functions.

36 Claims, 12 Drawing Sheets

(51) Int. Cl.
  *A61B 5/0205* (2006.01)
  *A61B 5/145* (2006.01)
  *H02J 7/00* (2006.01)
  *A61B 5/024* (2006.01)
  *A61B 5/0538* (2021.01)

(52) U.S. Cl.
  CPC ........ *A61B 5/14539* (2013.01); *A61B 5/4294* (2013.01); *A61B 5/4337* (2013.01); *H02J 7/0045* (2013.01); *A61B 5/024* (2013.01); *A61B 5/0538* (2013.01); *A61B 2010/0016* (2013.01); *A61B 2010/0019* (2013.01); *A61B 2010/0032* (2013.01); *A61B 2560/0214* (2013.01); *A61B 2560/0456* (2013.01)

(56) References Cited

U.S. PATENT DOCUMENTS

| | | | | |
|---|---|---|---|---|
| 5,247,932 | A * | 9/1993 | Chung | A61B 5/14542 600/338 |
| 5,444,254 | A * | 8/1995 | Thomson | G01T 1/161 250/370.07 |
| 9,031,645 | B2 | 5/2015 | Houben et al. | |
| 2002/0156394 | A1 * | 10/2002 | Mehrotra | A61D 17/002 128/903 |
| 2008/0071190 | A1 | 3/2008 | Gorodeski et al. | |
| 2010/0036213 | A1 * | 2/2010 | Rieth | A61B 5/01 600/301 |
| 2013/0041273 | A1 * | 2/2013 | Houben | A61B 5/7405 600/514 |
| 2015/0150753 | A1 * | 6/2015 | Racette | A61H 23/02 601/46 |
| 2016/0174946 | A1 * | 6/2016 | Sacks | G16Z 99/00 702/19 |
| 2017/0011210 | A1 * | 1/2017 | Cheong | A61B 5/681 |

OTHER PUBLICATIONS

Gould, Kenneth G., and Ansari, Amir H., Electrolyte Interactions in Cervical Mucus and Their Relationship to Circulating Hormone Levels, Contraception, May 1981, vol. 23, No. 5, pp. 507-516.

Albrecht, Bruce H., et al., A New Method for Predicting and Confirming Ovluation, Fertility and Sterility, Aug. 1985, vol. 44, No. 2, pp. 200-205.

Moreno, Jorge E., et al., Natural Family Planning: Suitability of the Cue Method for Defining the Time of Ovluation, Contraception, 1997, vol. 55, pp. 233-237.

Bigelow, Jamie L., et al., Mucus Observations in the Fertile Window: A Better Predictor of Conception Than Timing of Intercourse, Human Reproduction, 2004, vol. 19, No. 4, pp. 889-892.

Scarpa, Bruno, et al., Cervical Mucus Secretions on the Day of Intercourse: An Accurate Marker of Highly Fertile Days, European Journal of Obstetrics & Gynecology and Reproductive Biology, 2006, vol. 125, pp. 72-78.

Han, Leo, et al., Cervical Mucus and Contraception: What We Know and What We Don't, Contraception, 2017, vol. 96, pp. 310-321.

* cited by examiner

VAGINAL DEVICE AND METHOD FOR MEASURING FERTILITY-RELATED PARAMETER

PRIORITY CLAIM

The present application claims the priority benefit of U.S. provisional patent application No. 62/599,727 filed Dec. 17, 2017 and entitled "Vaginal Device," the disclosure of which is incorporated herein by reference.

SUMMARY

The present subject matter relates to vaginal devices. More particularly, the present subject matter relates to a vaginal device for monitoring a menstrual cycle.

A vaginal device configured to be inserted in a vagina of a user, the vaginal device comprising: a body comprising at least two electrodes configured to measure a fertility-related parameter of the user; a power source configured to provide power to the device; and an electrical system operably connected to the power source, the electrical system operably connected to one or more of the electrodes, the electrical system configured to switch one or more of the electrodes between charging and measuring functions.

A method for measuring a fertility-related parameter of a user includes: receiving the fertility-related parameter from a vaginal device, using a fertility-related parameter measurement system, the system comprising: a vaginal insertion device configured to be inserted in a vagina of the user, the vaginal device comprising: a body comprising at least two electrodes configured to measure a fertility-related parameter of the user; a power source configured to provide power to the device; and an electrical system operably connected to the power source, the electrical system operably connected to one or more of the electrodes, the electrical system configured to switch one or more of the electrodes between charging and measuring functions; relaying the fertility-related parameter to an external database system; receiving, from the external database system analysis of the fertility-related parameter by the external database system; and providing, to the user, fertility information using the system analysis.

DESCRIPTION OF THE DRAWINGS

The accompanying drawings provide visual representations which will be used to more fully describe various representative embodiments and can be used by those skilled in the art to better understand the representative embodiments disclosed herein and their inherent advantages. In these drawings, like reference numerals identify corresponding elements.

DETAILED DESCRIPTION

Figure 1:
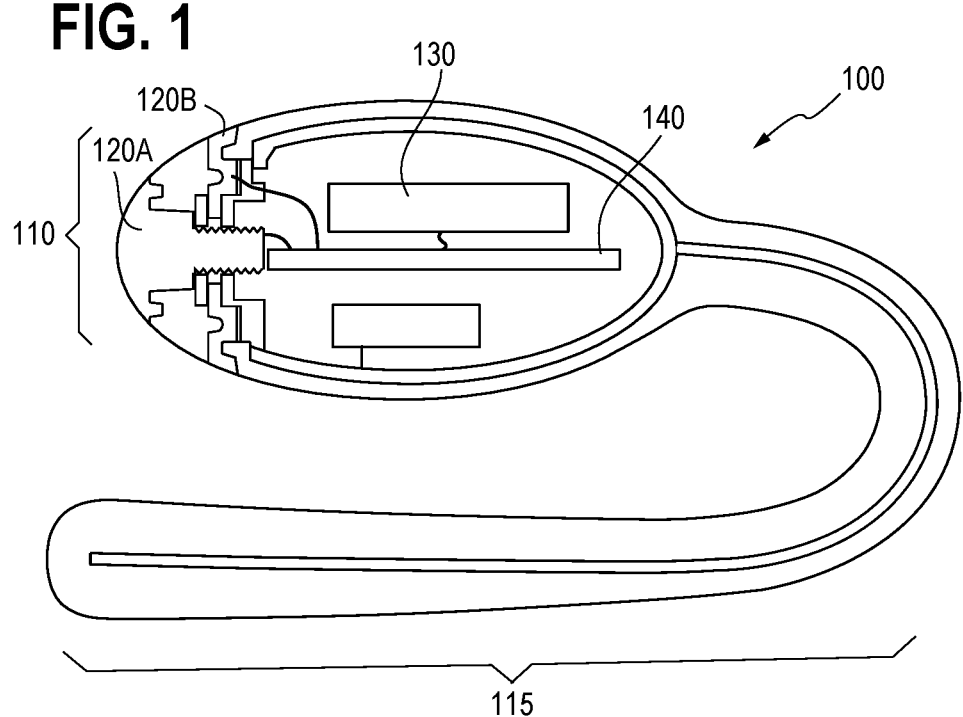
FIG. 1 is a cutaway drawing of a vaginal device.

While the present invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described. In the following description and in the several figures of the drawings, like reference numerals are used to describe the same, similar or corresponding parts in the several views of the drawings.

One aim of the present subject matter is to provide a vaginal device and methods for use thereof aimed at tracking fertility status relative to the day of ovulation of a user.

Another aim of the present subject matter is to provide a vaginal device and a method for use thereof aimed at tracking fertility status of a user.

Yet another aim of the present subject matter is to provide a vaginal device and a method for use thereof that preferably allow natural avoidance of unwanted pregnancy by providing a user data regarding her fertility status.

Still another aim of the present subject matter is to provide a vaginal device and a method for use thereof that allow a user to easily conceive by providing data regarding her fertility status.

An additional aim of the present subject matter is to provide a device and a method for use thereof that enable a user to detect an ovulatory cycle and monitor irregular menstrual cycles. An ovulation cycle event prediction system is provided for the purposes of providing information and recommendations to increase the chances of natural conception and/or natural contraception.

FIG. 1 is a cutaway drawing of a vaginal device 100 configured to be inserted in a user's vagina.

The vaginal device 100 comprises a body 110. For example, the body 110 comprises silicon. For example, the body is flexible. The vaginal device further comprises a tail 115, the tail 115 physically connected to the body 110.

The vaginal device 100 comprises a first electrode 120A and a second electrode 120B. Preferably, and as depicted, the body 110 comprises the first electrode 120A. For example, the first electrode 120A is positioned at or near an end of the body 110. For example, the second electrode 120B is positioned at or near an end of the body 110. As depicted, the first electrode 120A is positioned at the end of the body 110. Placement of one of the electrodes 120A-120B at or near the end of the body 110 makes possible measurements with the least variation in results.

Preferably, and as depicted, the body 110 comprises the second electrode 120B. For example, one or more of the first electrode 120A and the second electrode 120B is configured to measure a fertility-related parameter. For example, the fertility-related parameter comprises one or more of electrical impedance, basal body temperature, vaginal pH, heart rate, and another fertility-related parameter relating to the user's vaginal mucus. For example, the device uses one or more of the fertility-related parameters to compute a likelihood of pregnancy.

The vaginal device 100 further comprises a power source 130 operably connected to one or more of the first electrode 120A and the second electrode 120B, the power source 130 configured to provide power to the device. Preferably, and as depicted, the body 110 comprises the power source 130. Preferably, the power source 130 is operably connected to both the first electrode 120A and the second electrode 120B. For example, the power source 130 comprises a battery. For example, the power source 130 comprises a lithium ion battery.

The vaginal device 100 further comprises an electrical system 140, the electrical system operably connected to the power source 130, the electrical system operably connected to one or more of the first electrode 120A and the second electrode 120B. Preferably, and as depicted, the body 110 comprises the electrical system 140. Preferably, the electrical system 140 is operably connected to both the first electrode 120A and the second electrode 120B. The electrical system 140 is configured to control operation of the vaginal device 100. The electrical system 140 is configured to provide a safe, reliable electrical path.

One or more of the first electrode 120A and the second electrode 120B is configured to simultaneously execute charging and measuring. One or more of the first electrode 120A and the second electrode 120B is configured to function as a charge transfer mechanism whenever one or more of a sufficient voltage and a sufficient current is induced on these contacts.

The electrical system 140 is configured to switch one or more of the first electrode 120A and the second electrode 120B between charging and measuring functions.

For example, the electrodes 120A-120B are configured so that upon entry into the vagina, the electrodes 120A-120B will be in at least partial contact, and preferably in full contact, with vaginal fluids. For example, the body 110 of the vaginal device 100 is squeezable by the user.

Components of the vaginal device 100 that may be in contact with vaginal fluids, for example, one or more of the body 110, the first electrode 120A, and the second electrode 120B are one or more of resistant to humidity and substantially hum idity-proof.

Components of the vaginal device 100 that may be in contact with vaginal fluids, for example, one or more of the body 110, the first electrode 120A, and the second electrode 120B are one or more of water-resistant and substantially waterproof.

Optionally, the system further comprises an external database 150. For example, one or more of the fertility-related parameters and other data generated by the device can be transmitted to the external database 150. For example, analysis performed by the external database 150 may be more precise than internal analysis by the device.

Optionally, the vaginal device further comprises a communication system 160 configured to transmit one or more of a fertility-related parameter and other data generated by the device to the external database 150. For example, the communication system 160 is further configured to receive data from the external database 150. For example, the communication system 160 comprises a wireless communication system. For example, the communication system 160 uses Bluetooth.

Figure 2:
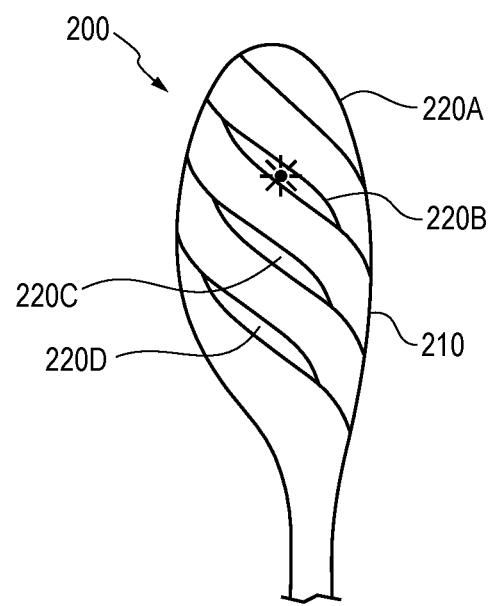
FIG. 2 is a cutaway schematic drawing of a vaginal device.

FIG. 2 is a cutaway schematic drawing of a vaginal device 200. The vaginal device 200 comprises a body 210. Attached to the surface of the body 210 are a plurality of electrodes 220A-220D. As depicted, attached to the surface of the body 210 are a first electrode 220A, a second electrode 220B, a third electrode 220C, and a fourth electrode 220D. For example, one or more of the first electrode 220A, the second electrode 220B, the third electrode 220C, and the fourth electrode 220D comprises a screw. Preferably, but not necessarily, the first electrode 220A comprises a screw.

The electrodes 220A-220D are configured to measure diverse fertility-related parameters of a user's body. For example, the electrodes 220A-220D are configured to measure diverse fertility-related parameters relating to the user's vaginal mucus. For example, the fertility-related parameter comprises one or more of electrical impedance, basal body temperature, vaginal pH, heart rate, and another fertility-related parameter relating to the user's vaginal mucus. For example, the device uses one or more of the fertility-related parameters to compute a likelihood of pregnancy.

As depicted, the first electrode 220A comprises a generally cap-like structure that is attached to an edge of the body 210. As depicted, the second electrode 220B comprises a ring-like electrode that is diagonally attached to a surface of the body 210. As depicted, the third electrode 220C comprises a ring-like electrode that is diagonally attached to a surface of the body 210. As depicted, the fourth electrode 220D comprises a ring-like electrode that is diagonally attached to a surface of the body 210.

As depicted, the electrodes 220A-220D are each physically continuous. Alternatively, at least one of the electrodes 220A-220D comprises a plurality of electrode dots closely attached on the surface of the body 210, forming patterns on the surface of the body 210, for example stripes similar to the ones depicted.

According to one embodiment, the electrodes 220A-220D may be made of any material known in the art that allows measurement of electrical impedance, for example but not limited to, metal, stainless steel, gold and the like.

According to another embodiment, one or more of the body 210 and the electrodes 220A-220D are made of a biocompatible material, thus allowing safe contact of the vaginal device 200 with a body of a user, particularly the user's vaginal tissue.

The electrodes 220A-220D may be placed anywhere on the body 210 of the vaginal device 200, for example, as depicted on the entire surface of the body 210.

For example, the electrodes 220A-220D are configured so that upon entry into the vagina, the electrodes 220A-220D will be in at least partial contact, and preferably in full contact, with vaginal fluids. For example, the body 210 of the vaginal device 200 is squeezable by the user.

Components of the vaginal device 200 that may be in contact with vaginal fluids, for example, one or more of the body 210, the first electrode 220A, the second electrode 220B, the third electrode 220C, and the fourth electrode 220D are one or more of resistant to humidity and substantially humidity-proof.

Components of the vaginal device 200 that may be in contact with vaginal fluids, for example, one or more of the body 210, the first electrode 220A, the second electrode 220B, the third electrode 220C, and the fourth electrode 220D is one or more of water-resistant and substantially waterproof.

Figure 3:
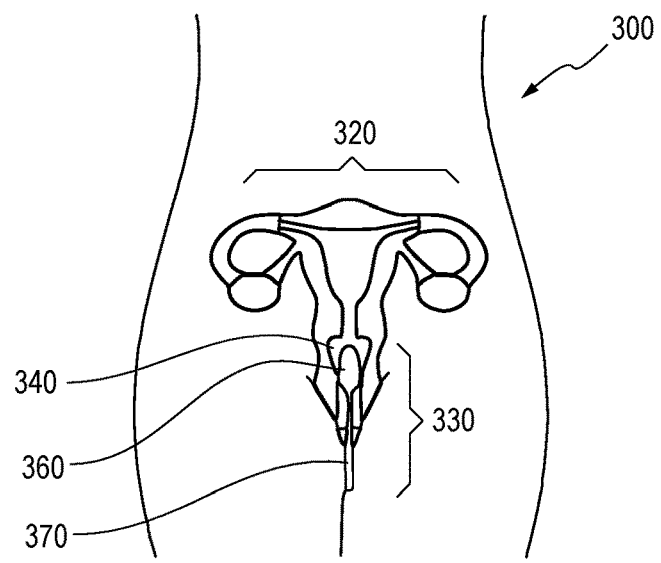
FIG. 3 is a schematic drawing showing a front view of a vaginal device inserted in a vagina of a human female body.

FIG. 3 is a schematic drawing of a front view 300 of a vaginal device 300 inserted in a vagina 320 of a user's body 330.

FIG. 3 schematically illustrates, according to an exemplary embodiment, a front view of a user's human female body 300 showing the female reproductive organs 320 and the vaginal device 330 inserted in the vagina 350. As depicted, the vaginal device 330 comprises a head 360 and a tail 370. As can be seen in FIG. 3, the head 360 of the vaginal device 330 is inserted into the vagina 350, while the tail 370 protrudes from the opening of the vagina 350 in a manner that allows holding of the tail 370 and pulling the vaginal device 330 out of the vagina 350.

Figure 4:
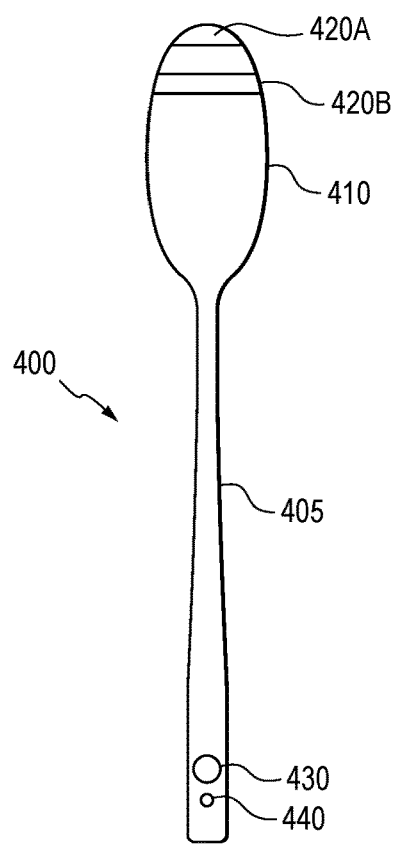
FIG. 4 is a schematic drawing of a vaginal device comprising a rigid tail.

FIG. 4 is a schematic drawing of a vaginal device 400 comprising a rigid tail 405. As depicted, the tail 405 is straight and rigid. Alternatively, or additionally, the tail 405 may be rigid and curved. Alternatively, or additionally, the tail 405 may be flexible, made for example of a wire-like material.

The vaginal device 400 further comprises a body 410 to which the tail 405 is attached. Attached to the surface of the body 410 are a first electrode 420A and a second electrode 420B.

The tail 405 is configured to be held by a user to facilitate one or more of insertion of the vaginal device 400 into the user's vagina (not shown) and removal of the vaginal device 400 from the vagina. Alternatively, or additionally, the tail 405 is configured to serve as an antenna for wireless communication, for example, Bluetooth.

The electrodes 420A and 420B are again configured to measure diverse fertility-related parameters of a user's body. For example, one or more of the first electrode 420A and the second electrode 420B is configured to measure a fertility-related parameter relating to the user's vaginal mucus. For example, the fertility-related parameter comprises one or more of electrical impedance, basal body temperature, vaginal pH, heart rate, and another fertility-related parameter relating to the user's vaginal mucus. For example, the device uses one or more of the fertility-related parameters to compute a likelihood of pregnancy.

As depicted, the first electrode 420A comprises a generally cap-like structure that is attached to an edge of the body 410. As depicted, the second electrode 420B comprises a ring-like electrode that is horizontally attached to a surface of the body 410. For example, one or more of the first electrode 420A and the second electrode 420B comprises a screw. Preferably, but not necessarily, the first electrode 420A comprises a screw.

As depicted, the electrodes 420A-420B are each physically continuous. Alternatively, at least one of the electrodes 420A-420B comprises a plurality of electrode dots closely attached on the surface of the body 410, forming patterns on the surface of the body 410, for example stripes similar to the ones depicted.

According to one embodiment, the electrodes 420A-420B may be made of any material known in the art that allows measurement of electrical impedance, for example but not limited to, metal, stainless steel, gold and the like.

According to another embodiment, one or more of the body 410 and the electrodes 420A-420B are made of a biocompatible material, thus allowing safe contact of the vaginal device 400 with a body of a user, particularly the user's vaginal tissue.

The electrodes 420A-420B may be placed anywhere on the body 410 of the vaginal device 400, for example, as depicted on the entire surface of the body 410. Preferably, although not necessarily, as depicted, the electrodes 420A-420B are placed on a top part of the body 410.

For example, the electrodes 420A-420B are configured so that upon entry into the vagina, the electrodes 420A-420B will be in at least partial contact, and preferably in full contact, with vaginal fluids. For example, the body 410 of the vaginal device 400 is squeezable by the user.

The vaginal device 400 further comprises an on/off button 430. As depicted, the on/off button 430 is positioned on the tail 405. Preferably, although not necessarily, the on/off button 430 is positioned on a part of the tail 405 that is not inserted into the vagina. As depicted, the on/off button 430 is positioned on a distal side of the tail 405 relative to the body 410. The on/off button 430 is configured to be pressable or movable by a user to do one or more of turn on the vaginal device 400 and turn off the vaginal device 400.

As depicted, the vaginal device 400 further comprises an optional light signal 440. For example, as depicted, the light signal 440 is positioned on the tail 405. Preferably, although not necessarily, the light signal 440 is positioned on a part of the tail 405 that is not inserted into the vagina (not shown). As depicted, the light signal 440 is positioned on a distal side of the tail 405 relative to the body 410. The light signal 440 is configured to indicate whether the vaginal device 400 is turned on or off. For example, the light signal 440 may comprise a light source emitting colored light indicating the on/off state of the vaginal device 400. For example, the light signal 440 may emit green light when the vaginal device 400 is turned on, and may emit red light when the vaginal device 400 is turned off.

Components of the vaginal device 400 that may be in contact with vaginal fluids, for example, one or more of the body 410, the first electrode 420A, the second electrode 420B, and at least a part of the tail 405 that is inserted into the vagina (not shown) are one or more of resistant to humidity and substantially humidity-proof.

Components of the vaginal device 400 that may be in contact with vaginal fluids, for example, one or more of the body 410, the first electrode 420A, the second electrode 420B, and at least a part of the tail 405 that is inserted into the vagina (not shown) are one or more of water-resistant and substantially waterproof.

Figure 5:
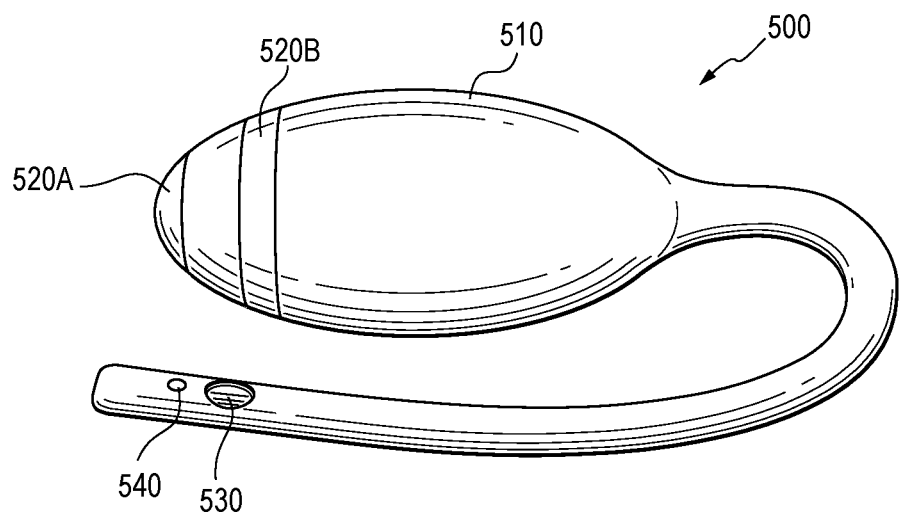
FIG. 5 is a drawing of a vaginal device comprising a rigid tail.

FIG. 5 is a drawing of a vaginal device 500 comprising a rigid tail 505. As depicted, the tail 505 is one or more of straight and rigid.

The vaginal device 500 further comprises a body 510 to which the tail 505 is attached. Attached to the surface of the body 510 are a first electrode 520A and a second electrode 520B.

The tail 505 is again configured to be held by a user to facilitate one or more of insertion of the vaginal device 500 into the user's vagina (not shown) and removal of the vaginal device 500 from the vagina. Alternatively, or additionally, the tail 505 is again configured to serve as an antenna for wireless communication, for example Bluetooth.

The electrodes 520A and 520B are again configured to measure diverse fertility-related parameters of a user's body. For example, one or more of the first electrode 520A and the second electrode 520B is configured to measure a fertility-related parameter relating to the user's vaginal mucus. For example, the fertility-related parameter comprises one or more of electrical impedance, basal body temperature, vaginal pH, heart rate, and another fertility-related parameter relating to the user's vaginal mucus. For example, the device uses one or more of the fertility-related parameters to compute a likelihood of pregnancy.

As depicted, the first electrode 520A comprises a generally cap-like structure that is attached to an edge of the body 510. As depicted, the second electrode 520B comprises a ring-like electrode that is horizontally attached to a surface of the body 510. For example, one or more of the first electrode 520A and the second electrode 520B comprises a screw. Preferably, but not necessarily, the first electrode 520A comprises a screw.

The vaginal device 500 further comprises an on/off button 530. As depicted, the on/off button 530 is positioned on the tail 505. Preferably, although not necessarily, the on/off button 530 is positioned on a part of the tail 505 that is not inserted into the vagina. As depicted, the on/off button 530 is positioned on a distal side of the tail 505 relative to the body 510. The on/off button 530 is configured to be pressable or movable by a user to do one or more of turn on the vaginal device 500 and turn off the vaginal device 500.

As depicted, the vaginal device 500 further comprises an optional light signal 540. For example, as depicted, the light signal 540 is positioned on the tail 505. Preferably, although not necessarily, the light signal 540 is positioned on a part of the tail 505 that is not inserted into the vagina (not shown). As depicted, the light signal 540 is positioned on a distal side of the tail 505 relative to the body 510. The light signal 540 is configured to indicate whether the vaginal device 500 is turned on or off. For example, the light signal 540 may comprise a light source emitting colored light indicating the on/off state of the vaginal device 500. For example, the light signal 540 may emit green light when the vaginal device 500 is turned on, and may emit yellow light when the vaginal device 500 is turned off.

As depicted, the electrodes 520A-520B are each physically continuous. Alternatively, at least one of the electrodes 520A-520B comprises a plurality of electrode dots closely attached on the surface of the body 510, forming patterns on the surface of the body 510, for example stripes similar to the ones depicted.

According to one embodiment, the electrodes 520A-520B may be made of any material known in the art that allows measurement of electrical impedance, for example but not limited to, metal, stainless steel, gold, and the like.

According to another embodiment, one or more of the body 510 and the electrodes 520A-520B are made of a biocompatible material, thus allowing safe contact of the vaginal device 500 with a body of a user, particularly the user's vaginal tissue.

The electrodes 520A-520B may be placed anywhere on the body 510 of the vaginal device 500, for example, as depicted on the entire surface of the body 510. Preferably, although not necessarily, as depicted, the electrodes 520A-520B are placed on a top part of the body 510.

For example, the electrodes 520A-520B are configured so that upon entry into the vagina, the electrodes 520A-520B will be in at least partial contact, and preferably in full contact, with vaginal fluids. For example, the body 510 of the vaginal device 500 is squeezable by the user.

Figure 6:
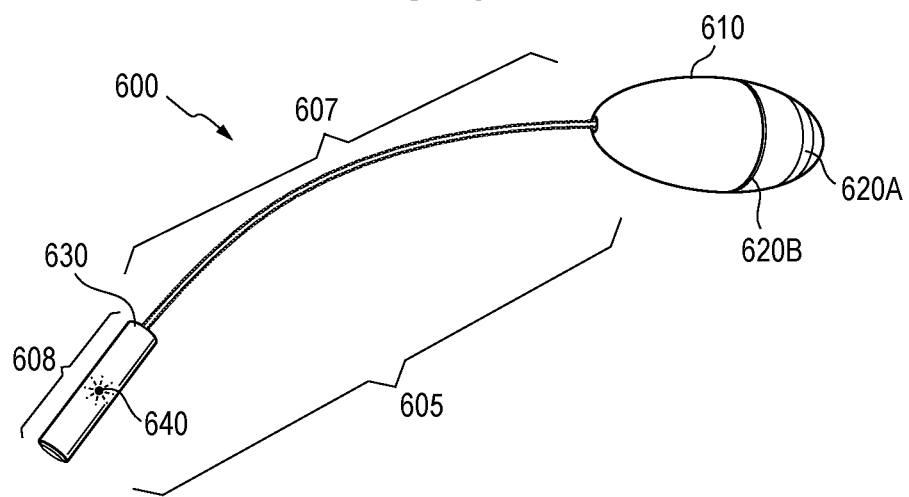
FIG. 6 is a drawing of a vaginal device comprising a tail.

FIG. 6 is a drawing of a vaginal device 600 comprising a tail 605. As depicted, the tail 605 is flexible and curved. For example, the tail 605 comprises one or more of metal and another wire-like material. The tail 605 comprises a medial tail portion 607. The tail 605 further comprises a distal tail portion 608. As depicted, the medial tail portion 607 is substantially flexible. As depicted, the distal tail portion 608 is substantially rigid.

The vaginal device 600 further comprises a body 610 to which the tail 605 is attached. Attached to the surface of the body 610 are a first electrode 620A and a second electrode 620B.

The tail 605 is again configured to be held by a user to facilitate one or more of insertion of the vaginal device 600 into the user's vagina (not shown) and removal of the vaginal device 600 from the vagina. More specifically, the distal tail portion 608 is configured to be held by a user to facilitate one or more of insertion of the vaginal device 600 into the user's vagina (not shown) and removal of the vaginal device 600 from the vagina. Alternatively, or additionally, the tail 605 is again configured to serve as an antenna for wireless communication, for example Bluetooth. More specifically, the distal tail portion 608 is configured to serve as an antenna for wireless communication, for example Bluetooth.

The electrodes 620A and 620B are again configured to measure diverse fertility-related parameters of a user's body. For example, one or more of the first electrode 620A and the second electrode 620B is configured to measure a fertility-related parameter relating to the user's vaginal mucus. For example, the fertility-related parameter comprises one or more of electrical impedance, basal body temperature, vaginal pH, heart rate, and another fertility-related parameter relating to the user's vaginal mucus. For example, the device uses one or more of the fertility-related parameters to compute a likelihood of pregnancy.

As depicted, the first electrode 620A comprises a generally cap-like structure that is attached to an edge of the body 610. As depicted, the second electrode 620B comprises a ring-like electrode that is horizontally attached to a surface of the body 610. For example, one or more of the first electrode 620A and the second electrode 620B comprises a screw. Preferably, but not necessarily, the first electrode 620A comprises a screw.

The vaginal device 600 further comprises an on/off button 630. As depicted, the on/off button 630 is positioned on the tail 605. Preferably, although not necessarily, the on/off button 630 is positioned on a part of the tail 605 that is not inserted into the vagina. As depicted, the on/off button 630 is positioned on the distal tail portion 608. The on/off button 630 is configured to be pressable or movable by a user to do one or more of turn on the vaginal device 600 and turn off the vaginal device 600.

As depicted, the vaginal device 600 further comprises an optional light signal 640. For example, as depicted, the light signal 640 is positioned on the tail 605. Preferably, although not necessarily, the light signal 640 is positioned on a part of the tail 605 that is not inserted into the vagina (not shown). As depicted, the light signal 640 is positioned on the distal tail portion 608. The light signal 640 is configured to indicate whether the vaginal device 600 is turned on or off. For example, the light signal 640 may comprise a light source emitting colored light indicating the on/off state of the vaginal device 600. For example, the light signal 640 may emit green light when the vaginal device 600 is turned on, and may emit yellow light when the vaginal device 600 is turned off.

As depicted, the electrodes 620A-620B are each physically continuous. Alternatively, at least one of the electrodes 620A-620B comprises a plurality of electrode dots closely attached on the surface of the body 610, forming patterns on the surface of the body 610, for example stripes similar to the ones depicted.

As depicted, the electrodes 620A-620B are each physically continuous. Alternatively, at least one of the electrodes 620A-620B comprises a plurality of electrode dots closely attached on the surface of the body 610, forming patterns on the surface of the body 610, for example stripes similar to the ones depicted.

According to one embodiment, the electrodes 620A-620B may be made of any material known in the art that allows measurement of electrical impedance, for example but not limited to, metal, stainless steel, gold and the like.

According to another embodiment, one or more of the body 610 and the electrodes 620A-620B are made of a biocompatible material, thus allowing safe contact of the vaginal device 600 with a body of a user, particularly the user's vaginal tissue.

The electrodes 620A-620B may be placed anywhere on the body 610 of the vaginal device 600, for example, as depicted on the entire surface of the body 610. Preferably, although not necessarily, as depicted, the electrodes 620A-620B are placed on a top part of the body 610.

For example, the electrodes 620A-620B are configured so that upon entry into the vagina, the electrodes 620A-620B will be in at least partial contact, and preferably in full contact, with vaginal fluids. For example, the body 610 of the vaginal device 600 is squeezable by the user.

Figure 7:
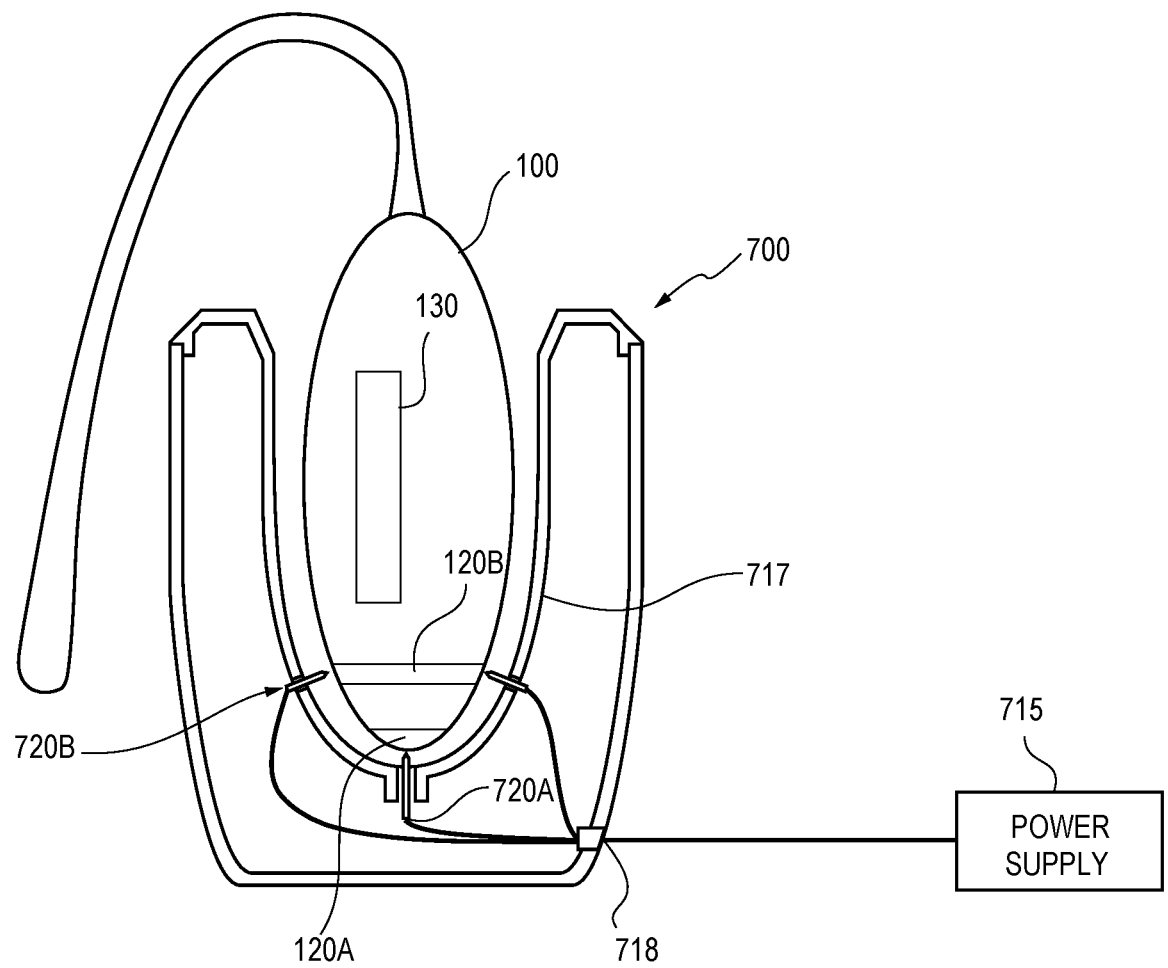
FIG. 7 is a drawing of a system for operating a vaginal device.

FIG. 7 is a drawing of a system 700 for operating a vaginal device 100. As above in FIG. 1, the vaginal device 100 comprises the first electrode 120A, the second electrode 120B, and the power source 130. The system 700 comprises a vaginal device 100 and a charging cradle 710 configured to do one or more of protect the vaginal device 100 and hold the vaginal device 100 in place for charging. The charging cradle 710 is operably connected to an external power supply 715. The charging cradle 710 further comprises a charging interface 717 configured to electrically connect with and charge at least one of the electrodes 120A-120B. The charging cradle 710 is configured to charge the power source 130 of the vaginal device 100 through the charging interface 717. The charging cradle 710 further comprises a power port 718. The power port 718 is configured to receive power from the external power supply 715.

For example, the external power supply 715 comprises a direct current (DC) power supply. As depicted, the charging interface 717 comprises three charging nodes 720A, 720B and 720C. The three charging nodes 720A-720C are configured to electrically connect with corresponding electrodes 120A-120B. As depicted, the first charging node 720A is configured to electrically connect with the first electrode 120A. The second charging node 720B and the third charging node 720C are both configured to electrically connect with the second electrode 120B. For example, one or more of the charging nodes 720A-720C is spring loaded. For example, one or more of the charging nodes 720A-720C comprises a pogo pin.

Figure 8:
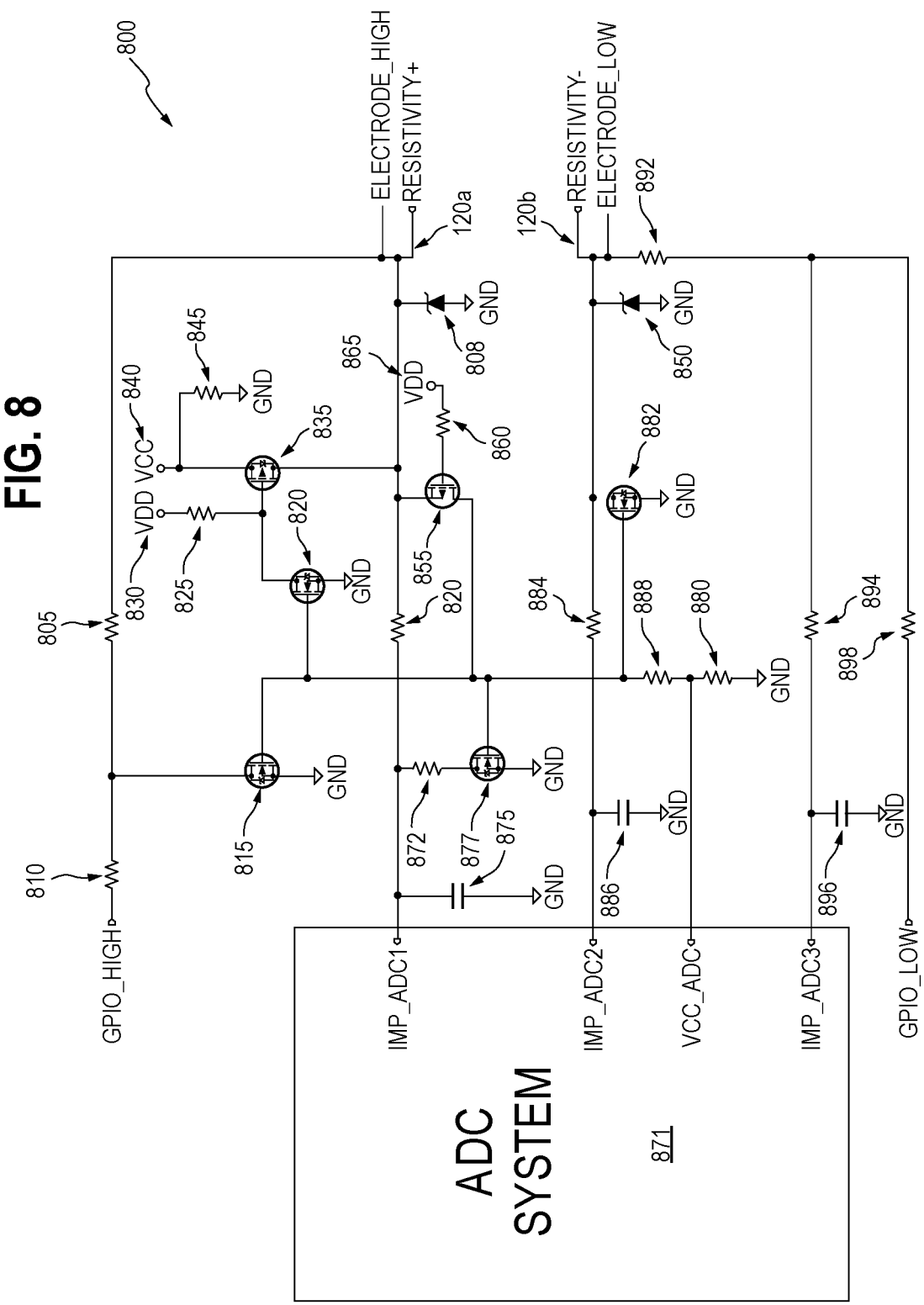
FIG. 8 is a schematic drawing of components of an interface system for a vaginal device.

FIG. 8 is a schematic drawing of components of an interface system 800 for a vaginal device.

The interface system 800 forms part of the electrical system 140 shown in FIG. 1. The interface system 800 comprises a network of transistors, capacitors, and resistors as shown in FIG. 8. For example, at least one of the transistors comprises a metal oxide semiconductor field effect transistors (MOSFET). For example, at least one of the capacitors comprises a low-pass filter capacitor. The low-pass filter capacitor increases a sensitivity of a measurement of the electrical impedance of the user's vaginal mucus.

The first electrode 120A and the second electrode 120B are operably connected to the interface system 800. For simplicity, they are shown in FIG. 8 as comprised in the interface system 800. As shown, the first electrode 120A is operably connected to a first resistor 805. The first resistor 805 is operably connected to a second resistor 810. The first resistor 805 is also operably connected to a first N-channel MOSFET 815, which is grounded. The first N-channel MOSFET 815 is operably connected to a second N-channel MOSFET 820, which is grounded. The second N-channel MOSFET 820 is operably connected to a third resistor 825. The third resistor 825 is operably connected to a regulated voltage (VDD) 830. The second N-channel MOSFET 820 is also operably connected to a first P-channel MOSFET 835. The first P-channel MOSFET 835 is operably connected to the first electrode 120A. The first P-channel MOSFET 835 is also operably connected to a charger input 840, also known as a voltage at the common collector (VCC). The first P-channel MOSFET 835 is also operably connected to a fourth resistor 845, which is grounded. The first electrode 120A is also operably connected to a first diode 850, which provides protection from electrostatic discharge (ESD). Use of diodes for ESD protection allows very low leakage current less than or equal to approximately 0.01 microAmperes (µA), permitting ESD protection without significantly affecting measurement of fertility-related parameters.

The first diode 850 is operably connected to a second P-channel MOSFET 855. The second P-channel MOSFET 855 is operably connected to a fourth resistor 860, which is grounded. The fourth resistor 860 is also operably connected to a second regulated voltage (VDD) 830A. The second P-channel MOSFET 855 is also operably connected to a fifth resistor 870, which is operably connected to a protecting resistor 872. The fifth resistor 870 is operably connected to an analog to digital converter (ADC) system 871. The fifth resistor 870 protects the ADC system 871. The protecting resistor 872 is also operably connected to a first capacitor 875, which is grounded. For example, the first capacitor 875 comprises a low pass filter capacitor. The protecting resistor 872 is also operably connected to a third N-channel MOSFET 877, which is grounded.

The second electrode 120B is also operably connected to a second diode 880, which provides protection from ESD. The second diode 880 is operably connected to a fourth N-channel MOSFET 882. The fourth N-channel MOSFET 882 is also operably connected to a sixth resistor 884. The sixth resistor 884 protects the ADC system 871. The sixth resistor 884 is operably connected to a second capacitor 886. For example, the second capacitor 886 comprises a low pass filter capacitor. The sixth resistor 884 is also operably connected to a seventh resistor 888. The seventh resistor 888 is operably connected to an eighth resistor 890.

The second electrode 120B is also operably connected to a reference resistor 892. The reference resistor 892 facilitates a comparison of 1) a voltage drop between the first electrode 120A and the second electrode 120B and 2) a voltage drop across the reference resistor 892. The reference resistor 892 is operably connected to a ninth resistor 894. The ninth resistor 894 is operably connected to a third capacitor 896. For example, the third capacitor 896 comprises a low pass filter capacitor. The reference resistor 892 is also operably connected to a current limiting resistor 898, used for limiting current.

When no external voltage is present on the electrodes 120A-120B, the P-channel MOSFETs 835 and 855 will both have a non-negative voltage from their respective gates to their respective sources. The P-channel MOSFETs 835 and 855 are held in state of non-negative voltage because the gates are connected to the regulated power source of the internal electrical system through resistors 825 and 860 and because the other interfaces from the internal electrical system are all drawn from this source it will never achieve a negative voltage from the gate to source without external voltage injection. In this state, the P-channel MOSFETs 835 and 855 are held in a high impedance state, which causes the net tied to the gates of N-channel MOSFETS 815, 877, 820 and 882 to be pulled to a zero voltage through resistors 888 and 890. This in turn leaves N-channel MOSFETs 815, 877, 820 and 882 also in a high impedance state. In this configuration, the internal electrical system is free to provide a current across the electrodes 120A and 120B without interference from the charging system. This causes a voltage to develop across the nodes at 120A and 120B related to the complex impedance of vaginal mucus connecting the nodes 120A and 120B externally and in turn allows for the ADC system 871 to directly measure this impedance. This configuration allows the electrical system to control the voltage present on the external contacts and prevent substantial interference to the ADC system 871 during mucus impedance measurement.

When an external voltage is applied across the nodes at 120A and 120B with the positive voltage apparent at 120A, the P-channel MOSFETs 835 and 855 will both have a voltage equal to the difference from their gate to source between the internal regulated power source 830 and the external power supply (not shown in this figure; item 715 in FIG. 7). As the external voltage increases above the internal regulated power source 830, this voltage becomes negative. At any voltage greater than a given voltage above the internal regulated power source 830, MOSFETs 835 and 855 will change to a low impedance state. This voltage is dependent on the individual specifications of the chosen MOSFETs for 835 and 855. In this state, the connection to the internal battery charging system is equal to the external voltage on electrode 120A through MOSFET 855 as it is in a low impedance state. The net tied to the gates of N-channel MOSFETS 815, 877, 820 and 882 is also pulled to be equal to the external voltage on electrode 120A through MOSFET 835 as it is in a low impedance state. In turn this causes N-channel MOSFETS 815, 877, 820 and 882 to be put into a low impedance state. Given that MOSFET 882 is in a low impedance state, the ground connection of the internal electrical system is now held at the same voltage level on electrode 120B. The internal battery charging system therefore has the external voltage across 120A and 120B applied to its power input with low impedance connections and allows significant current to pass through to the internal battery from the external source unimpeded. Simultaneously the two connections exposed to the high side of the voltage across 120A and 120B are brought to ground through MOSFETs 815 and 877. Coupled with the series resistances 805 and 810, this provides significant protection to these connections to the internal electrical system against the higher externally applied voltage.

Figure 9:
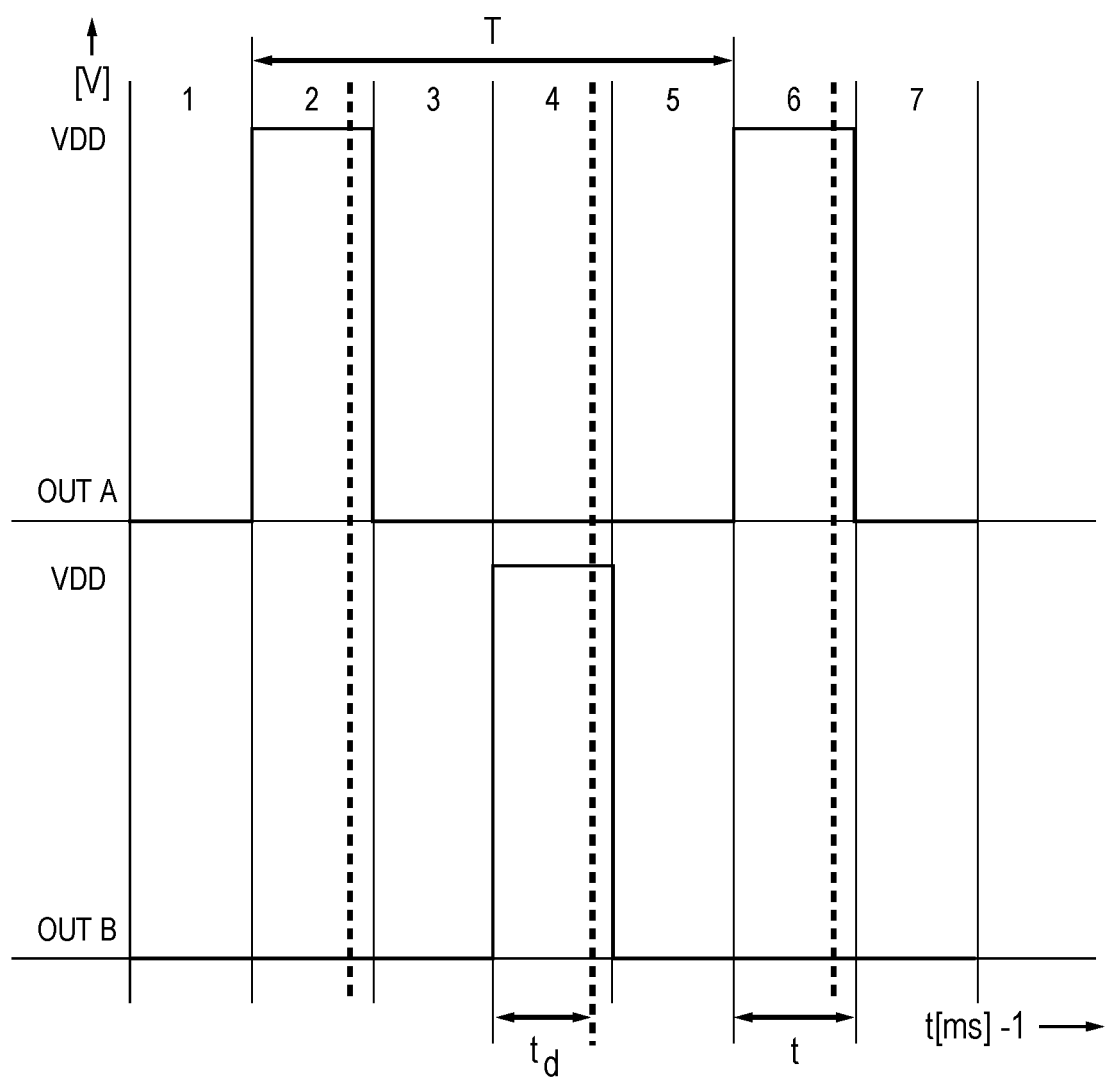
FIG. 9 is a graph showing voltage (V) over time (t) during measurements made by the vaginal device.

FIG. 9 is a graph showing representative measurements made by the vaginal device of voltage (regulated voltage or VDD, in volts) over time (t). T indicates the time period of repetition of measurements; t indicates voltage pulse width, namely the length of voltage pulse, and $t_d$ indicates sampling delay, namely the time between pulse start and sampling time.

According to one embodiment, the vaginal device measures bipolar resistivity of vaginal mucus. This is achieved by using alternating voltage pulses, which are led to electrodes via a resistor that is limiting the current. At the same time the resistor is limiting the current, it is also measuring the current. Using these data, the vaginal device calculates the electrical impedance of the vaginal mucus. Alternating current substantially prevents one or more of electrolytic dissolving of electrode plating, electrolytic coating of electrodes, and electrolytic decay of vaginal mucus.

Accuracy can be improved by use of multiple electrodes for one or more of resistive tomography and impedance tomography.

Figure 10:
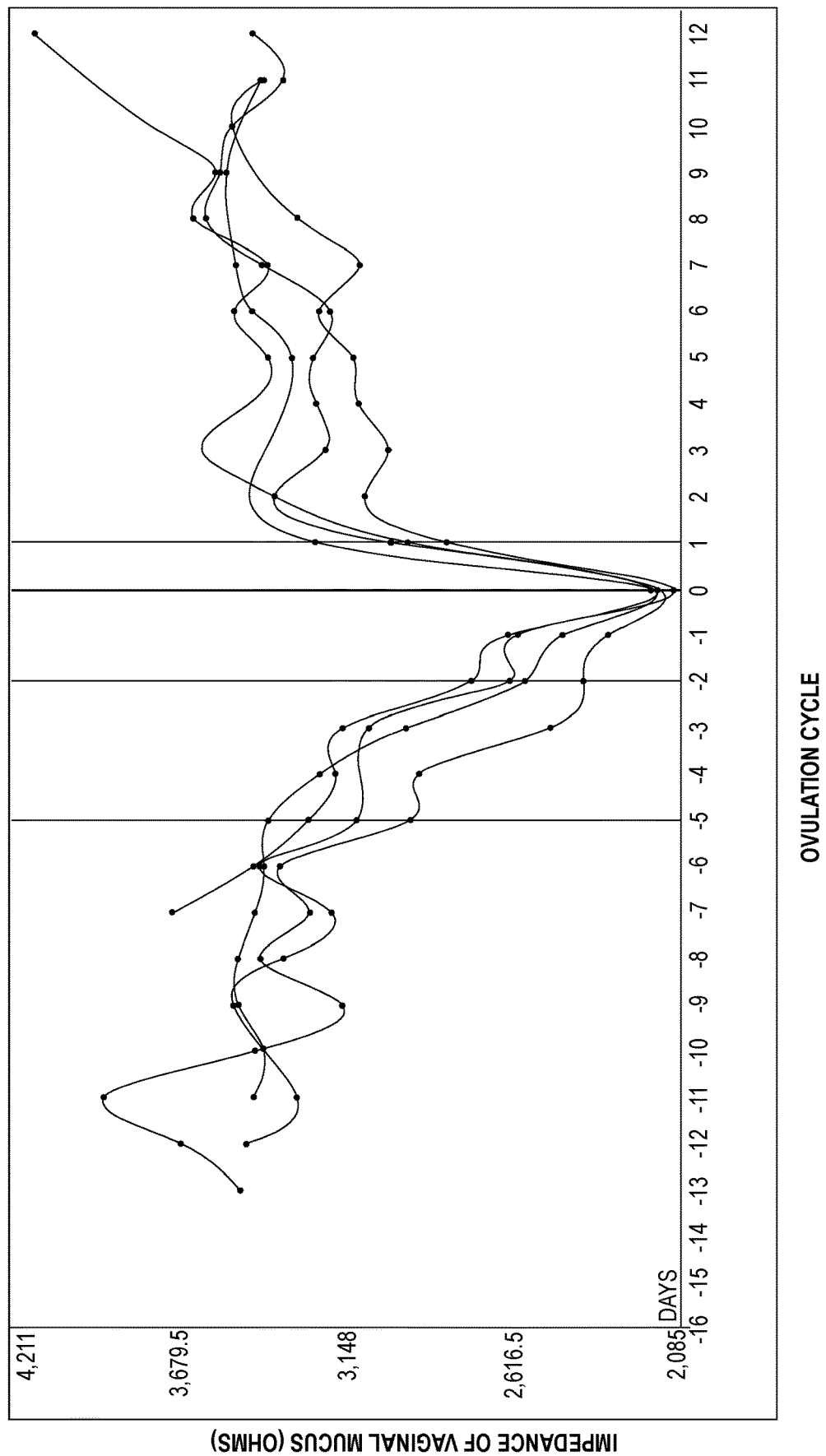
FIG. 10 presents a graph of impedance of vaginal mucus vs. day of ovulation cycle obtained by thirty women using the vaginal device.

FIG. 10 presents a graph of impedance of vaginal mucus (in ohms) vs. day of ovulation cycle obtained by a representative subset of at least thirty women using the vaginal device.

According to one embodiment, there is provided a computer program run on a computing device. Any type of computing device is under the scope of the present subject matter. According to a preferred embodiment, the computing device is a mobile computing device, for example a smartphone. The computing device is electronically connected to the vaginal device. According to another embodiment, there are provided a processor, a database and a memory configured to process and store data received by the computing device and transmit data to be displayed to a user either with the computing device or a dedicated display. The processor, the database and the memory may be positioned remotely from the computing device, while the computing device is configured to be used and activated by a user of the vaginal device, namely the computing device is configured to be positioned in the vicinity of the vaginal device. Furthermore, the processor, the database and the memory may be comprised in the cloud. According to one embodiment, the cloud is connected to the computing device.

According to one embodiment, the system is configured to predict menstrual cycles and more particularly predict ovulation and fertile period. According to this embodiment, the system collects a user's body data such as basal body temperature, vaginal pH—for example based on impedance of the vaginal fluids, heart rate and the like. The data are preferably collected every morning by inserting the vaginal device into the vagina for a certain period of time that is enough to collect the necessary data, for example substantially 5 minutes. The collected data are transferred to a mobile device, for example a smartphone. The smartphone runs a computer program, namely an application that processes the data, submits the data to a cloud, receives processed data from the cloud and displays the data to the user via the smartphone, for example. Thus, the application displays the user's measurements, cycles, last period and most importantly a prediction of one or more of a next ovulation time and a next period.

According to one embodiment, there is provided a dedicated application available for download and installation on a smartphone. Once the application is installed, the user is prompted to register into a user database. Next, the user is prompted to pair the application with the vaginal device. The vaginal device is configured to start automatically every time it is taken out from a charging station or every time it is pressed by a user. According to this embodiment, the vaginal device further comprises a power source, for example a battery, configured to supply power to the vaginal device.

According to one embodiment, every morning a user is prompted to turn on the vaginal device and to insert the vaginal device into the vagina. Then the user is prompted to start the application and open in the application a device tab. At this stage, the vaginal device is configured to synchronize automatically with the application. If synchronization does not happen, the user is prompted to make sure that a communication line between the smartphone and the vaginal device, for example Bluetooth, is turned on. Alternatively, the user may manually synchronize the vaginal device with the application by pressing a 'SYNC' button comprised in a device tab of the application. Once the vaginal device is inserted into the vagina, it is configured to begin measuring fertility-related parameters. This should take approximately 5 minutes.

During the measurement of the fertility-related parameters, the user may see the status of measurement in the Device Tab' of the application. Once the measurements are done, the user is prompted to the remove the vaginal device from the vagina.

After the vaginal device is removed from the vagina, it may be cleaned, for example, with water and soap and then dried. Then the vaginal device may be returned to a charging dock for charging the power source of the vaginal device until next time of usage. According to one embodiment, charging may take approximately 30 minutes.

Figure 11:
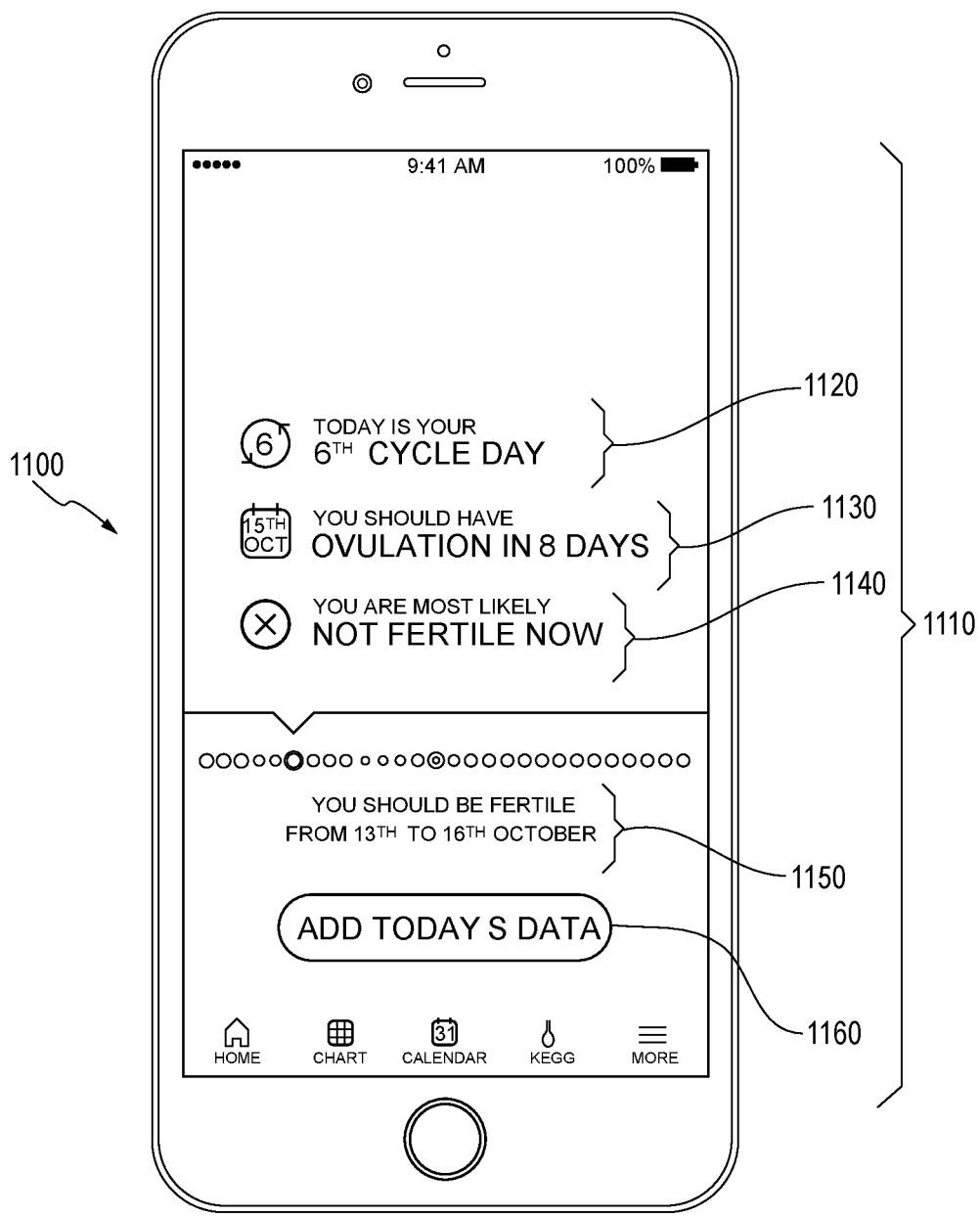
FIG. 11 illustrates an exemplary screenshot of a home page of an application configured to be used with the vaginal device.

FIG. 11 illustrates an exemplary screenshot of a home page of an application configured to be used with the vaginal device.

FIG. 11 depicts a mobile device 1100 of a user showing a screenshot of a home page 1110 of the application. The application is an interface where a user may find all her data collected from the vaginal device, cycle calendar and user's future predictions. The user may also control the vaginal device from the application.

FIG. 11 depicts a screenshot of the home page 1110 of the application. When the application is used for the first time, the user is prompted to create a profile in a database in order to store the user's measurements. Also, there is a need to collect some personal information like the user's last period, regularity of the user's cycles, age and the like, so predictions may be created as accurately as possible.

The home page 1110 is the main screen of the application. In the home page 1110, the user may see the most important information about her current cycle including a cycle day 1120, an ovulation prediction 1130, a current fertility window 1140, a next fertility window 1150, and a data addition button 1160.

The cycle day 1120 comprises a number of days from the user's most recent period. As depicted, the cycle day 1120 comprises the text, "Today is your $6^{th}$ cycle day."

The ovulation prediction 1130 comprises a prediction of one or more of a next ovulation for the user and a next period for the user. As depicted, the ovulation prediction 1130 comprises the text, "You should have ovulation in 8 days."

The current fertility window 1140 comprises a prediction as to a user's fertility. As depicted, the fertility window 1140 comprises the text, "You are most likely not fertile now."

The next fertility window 1150 comprises the text, "You are most likely not fertile now."

Figure 14:
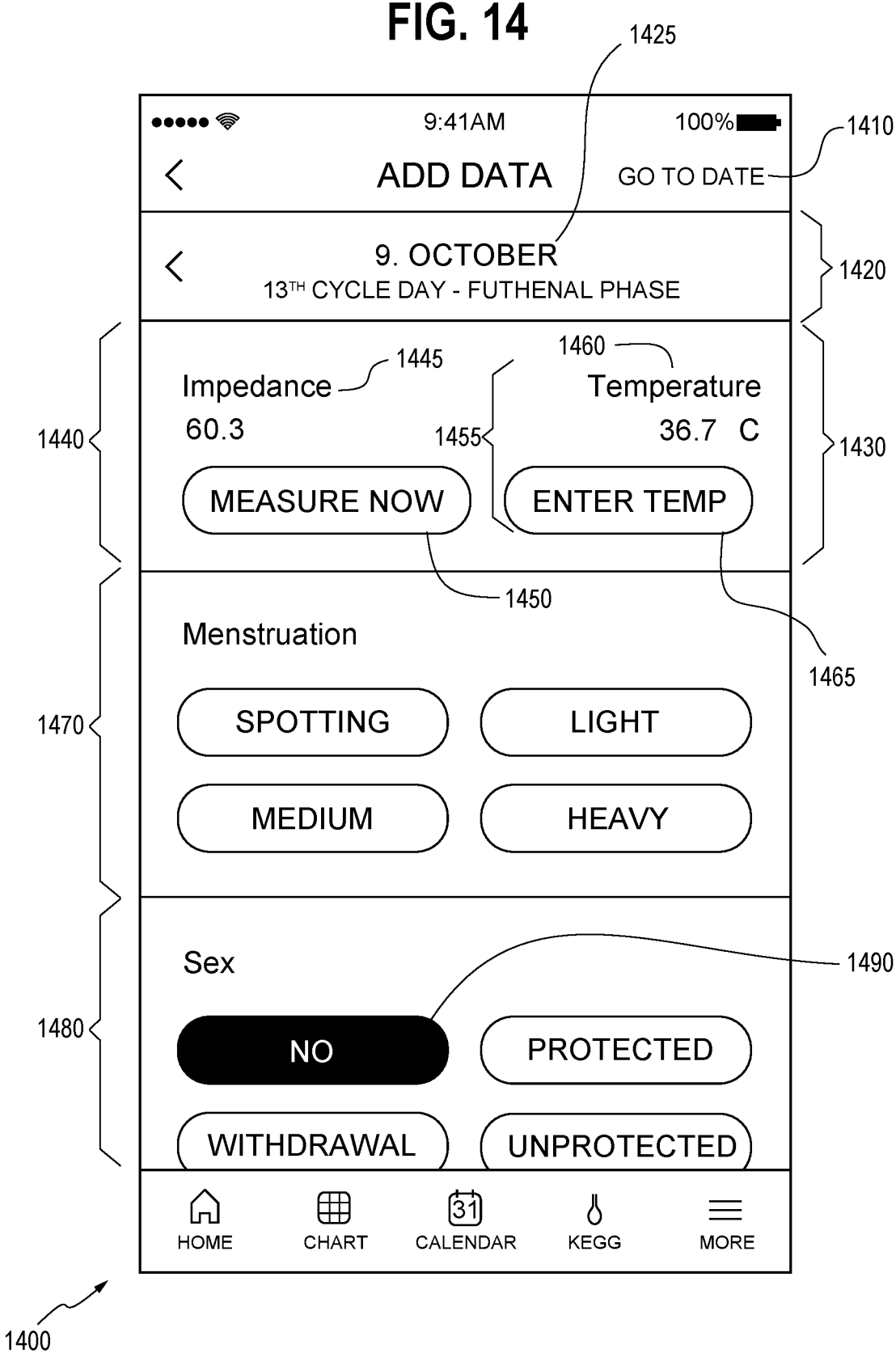
FIG. 14 illustrates an exemplary screenshot of a data addition page of an application configured to be used with the vaginal device.

The data addition button 1160 comprises the text, "Add today's data." If the user presses the data addition button 1160, the user is taken to the data addition page 1400 shown in FIG. 14 and is invited to input data into the mobile device 1100.

Figure 12:
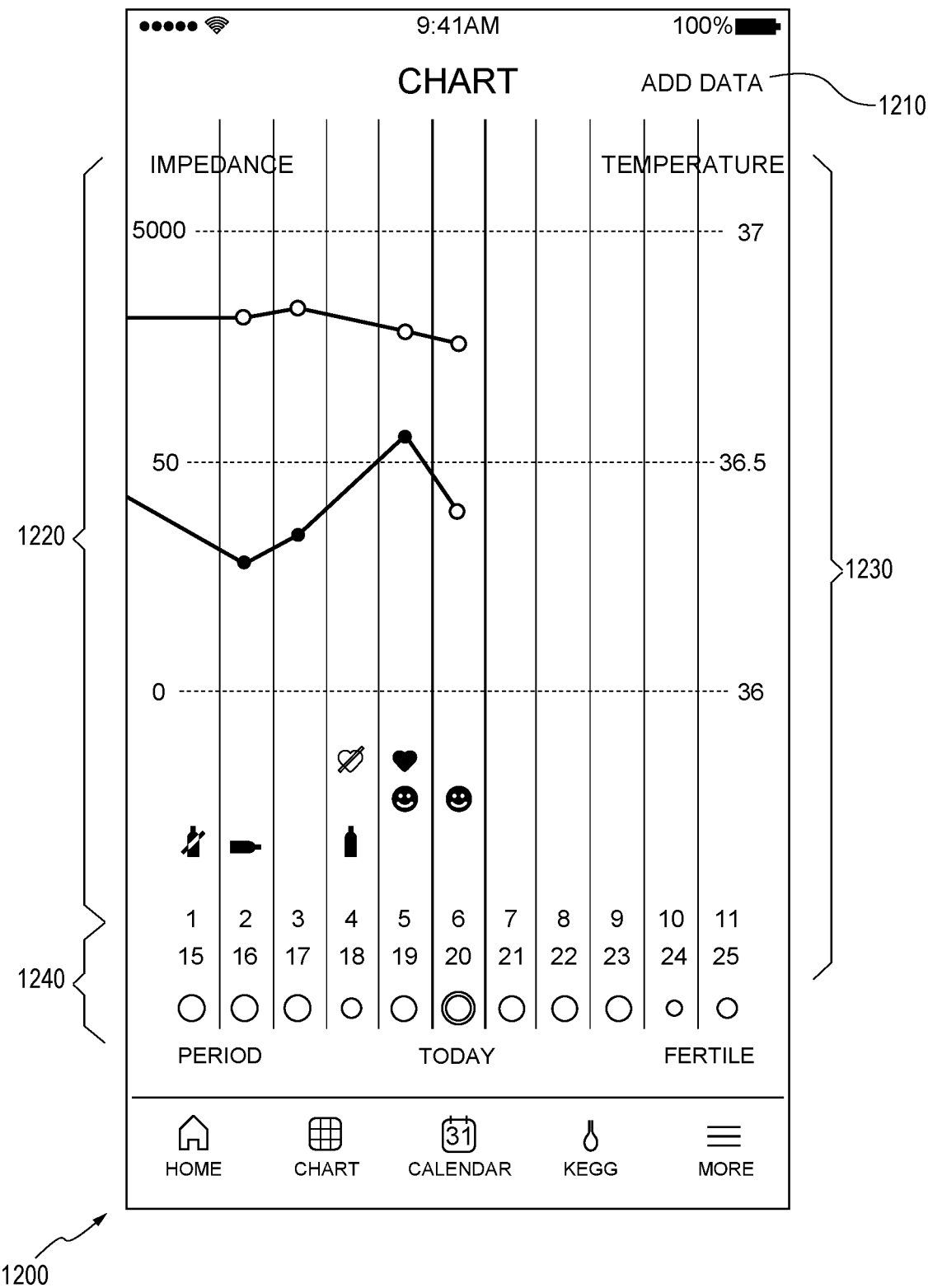
FIG. 12 illustrates an exemplary screenshot of a chart page of an application configured to be used with the vaginal device.

FIG. 12 illustrates an exemplary screenshot of a chart page 1200 of an application configured to be used with the vaginal device.

Included on the chart page 1200 are a data addition button 1210, an impedance record 1220 showing measured impedance of the user's vaginal mucus, a temperature record 1230 showing measured basal body temperatures of the user in Celsius, and a thumbnail calendar 1240. If the user presses the data addition button 1210, the user is taken to the data addition page 1400 shown in FIG. 14 and is invited to input data into the mobile device 1100.

The user has the option to select Fahrenheit instead of Celsius for the temperature record 1230. The thumbnail calendar 1240 displays the user's current fertility cycle, showing the day of the fertility cycle in which the user is today as day 20. The thumbnail calendar 1240 comprises a fertile period indicator. If the user clicks on the thumbnail calendar 1240, the user is taken to the calendar page 1300, shown in FIG. 13.

Figure 13:
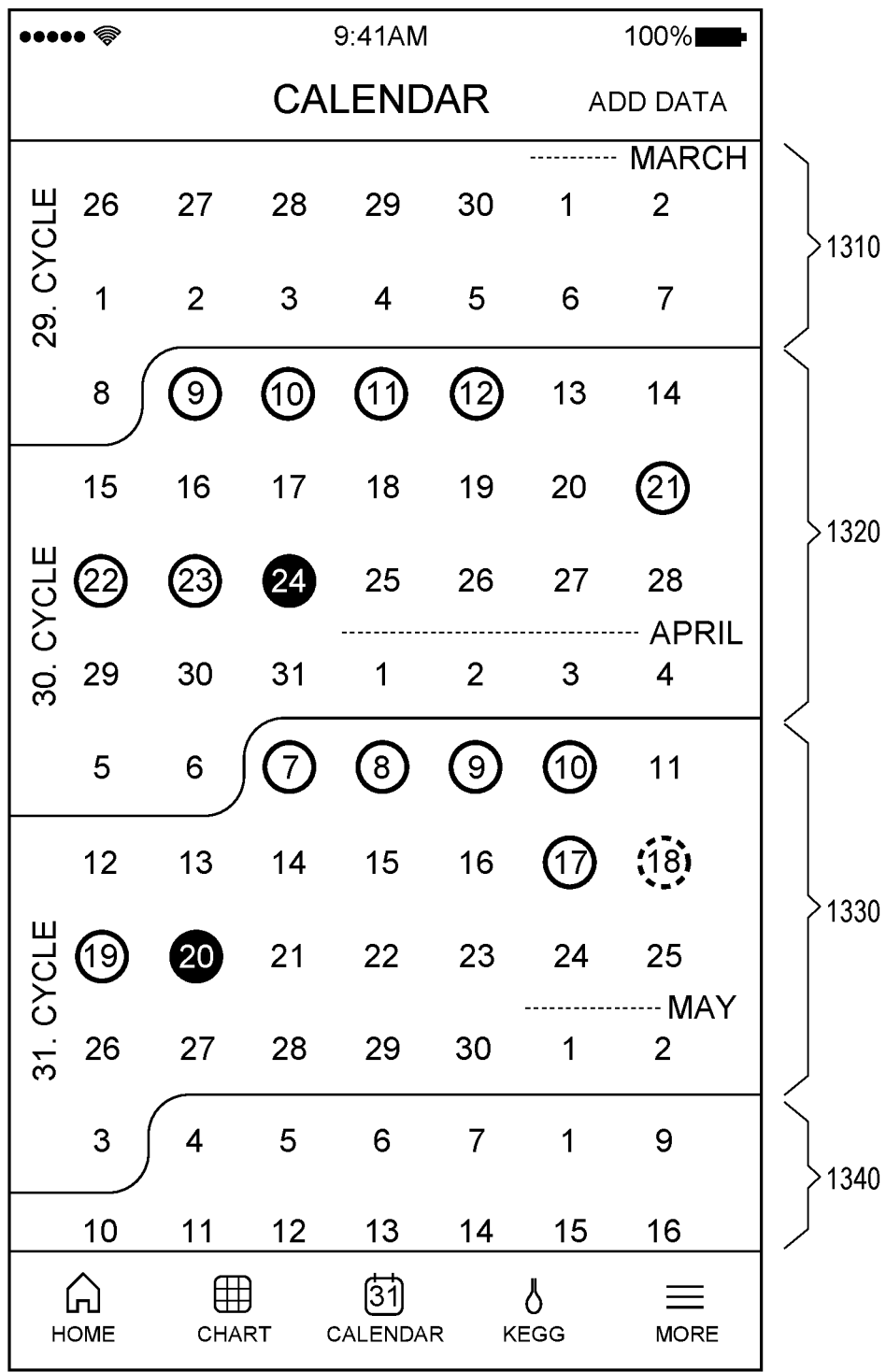
FIG. 13 illustrates an exemplary screenshot of a calendar page of an application configured to be used with the vaginal device.

FIG. 13 illustrates an exemplary screenshot of a calendar page 1300 of an application configured to be used with the vaginal device.

Depicted are graphical visualizations of parts of four user fertility cycles, a first fertility cycle 1310 for which only the latter 15 days are shown, a second fertility cycle 1320 shown in full, a third fertility cycle 1330 also shown in full, and a fourth fertility cycle 1340, for which only the first 13 days are shown. Days of each cycle are marked as appropriate as one or more of a fertile day, an infertile day, a day of ovulation, a day of a period, and a likely day to conceive. Both past fertility cycles and projected future fertility cycles can be viewed by the user using the calendar page 1300.

FIG. 14 illustrates an exemplary screenshot of a data addition page 1400 of an application configured to be used with the vaginal device.

The data addition page 1400 allows the user to data at any time regarding one or more of her body and any other pertinent issue. The data addition page 1400 provides a The data addition page 1400 prompts the user to provide manually additional data, for example, parameters like: mood, drinking, vaginal mucus, sex, and the like. The input of these data is optional, but the more data is added by the user, the more accurate the prediction will be.

As depicted, the data addition page 1400 comprises a "go to date" button 1410. If the user presses this "go to date" button 1410, she can go to any desired date of interest for which she desires to input data.

The data addition page 1400 further comprises a date window 1420 comprising the date of interest 1425, and also listing the day of the user's fertility cycle and the phase of the user's fertility cycle. As depicted, the date of interest 1425 shows a date of October 9. By default, the date window 1420 displays as the date of interest 1425 the current date and information on the current date.

The impedance and temperature window 1430 comprises a vaginal impedance window 1440 comprising an impedance value window 1445 showing the user's vaginal impedance on the date of interest 1425. As depicted, the impedance value window 1445 shows the user's vaginal impedance on October 9 as 60.3. The vaginal impedance window 1440 further comprises an impedance measurement button 1450 allowing the user to measure her vaginal impedance.

The impedance and temperature window 1430 further comprises a temperature window 1455 comprising a temperature value window 1460 showing the user's basal body temperature on the date of interest 1425. As depicted, the temperature value window 1455 shows the user's basal body temperature on October 9 as 36.7 degrees Celsius. The user has the option in the "Your Profile" page discussed below to select Fahrenheit instead of Celsius for the temperature window 1455. The temperature window 1455 further comprises a temperature measurement button 1465 allowing the user to measure her basal body temperature.

The data addition page 1400 further comprises a menstruation window 1470 that allows the user to choose a menstruation level as one or more of spotting, light, medium, and heavy. The user's selection is then indicated by an appropriate darkened bubble. As depicted, the user has not selected a menstruation level.

The data addition page 1400 further comprises a sex window 1480 that allows the user to choose a sexual activity level as one or more of no sexual activity, protected sex, withdrawal sex, and unprotected sex. The user's selection is then indicated by an appropriate darkened bubble. As depicted by the darkened "no sexual activity" button 1490, the user has selected a sexual activity level of no sexual activity.

A "Your Profile" page shows the user her personal information. Using buttons on this page, the user may modify profile information provided during registration for the application and/or subsequently to registration.

An "App Lock" page provides the user an opportunity to secure the application and the data with a personal identification number (PIN) code, so no one but the user may be able to access the application.

Figure 15:
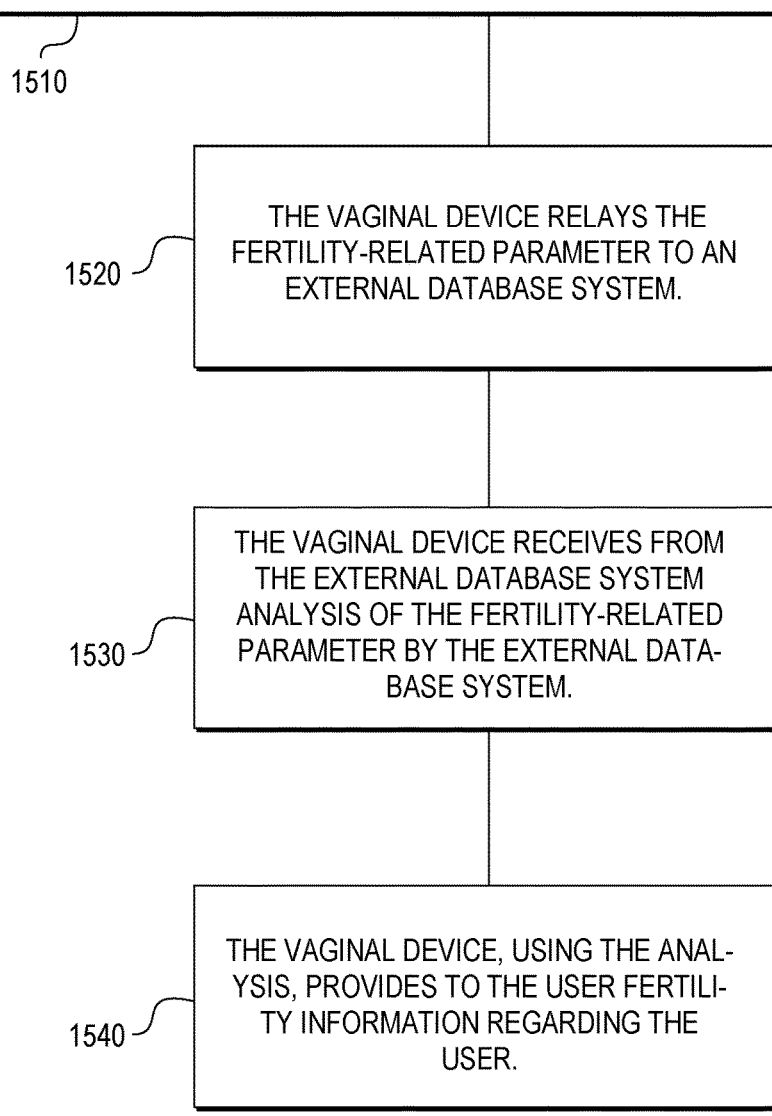
FIG. 15 is a flow chart of a method for measuring a fertility-related parameter of a user.

FIG. 15 is a flow chart of a method 1500 for measuring a fertility-related parameter of a user.

The order of the steps in the method 1500 is not constrained to that shown in FIG. 15 or described in the following discussion. Several of the steps could occur in a different order without affecting the final result. For example, one or more of the steps in the method is performed using a software system running on a user-operated mobile device.

In step 1510, a vaginal device configured to be inserted in a vagina of the user measures a fertility-related parameter of the user, the vaginal device comprising: a body comprising at least two electrodes configured to measure a fertility-related parameter of the user; a power source configured to provide power to the device; and an electrical system operably connected to the power source, the electrical system operably connected to one or more of the electrodes, the electrical system configured to switch one or more of the electrodes between charging and measuring functions. Block 1510 then transfers control to block 1520.

In step 1520, the vaginal device relays the fertility-related parameter to an external database system. Block 1520 then transfers control to block 1530.

In step 1530, the vaginal device receives from the external database system analysis of the fertility-related parameter by the external database system. Block 1530 then transfers control to block 1540.

In step 1540, using the system analysis, the vaginal device provides to the user fertility information regarding the user. For example, the fertility information comprises feedback to the user generated using one or more of the fertility-related parameters and the system analysis. For example, the feedback comprises information regarding one or more of natural conception and natural contraception. For example, the system analysis comprises a timing estimate obtained using an algorithm configured to estimate a timing of an ovulation cycle of the user. Block 1540 then terminates the process.

According to one embodiment, as described herein, the vaginal device and the system comprising the vaginal device are configured to be used by humans. According to another embodiment, the vaginal device and the system comprising the vaginal device may be used with animals, for example, sheep, bovine, and the like.

As is evident from FIG. 9, an advantage of the invention is more accurate determination of whether the user is pregnant or not. By contrast, prior art methods, that measure one or more of Luteinizing Hormone (LH), progesterone, estradiol, and basal body temperature (B. B. T.), measure secondary rather than primary characteristics of pregnancy and are not as fully indicative of the fertile period.

Another advantage of the invention is to allow the two electrodes to simultaneously perform functions of measurement and contact charging.

Other advantages of the invention include the vaginal device of the present subject matter monitors electrical impedance of vaginal mucus, in other words, monitors the cause of fertility. Therefore, in contract to prior art devices and methods, the vaginal device of the present subject matter indicates the female fertility period more accurately than prior art devices and methods.

Further advantages of the invention include that the placement of an electrode at or near an end of the body of the vaginal device makes possible measurements with the least variation in results.

A still further advantage of the invention is that it allows the electrical system to control the voltage present on the external contacts and prevent substantial interference to the internal ADC measuring system during mucus impedance measurement.

Another advantage of the invention is that the low pass filters allow more precise measurement of fertility-related parameters including impedance of vaginal mucus.

Still another advantage is that use of diodes for ESD protection allows very low leakage current, permitting ESD protection without significantly affecting measurement of fertility-related parameters.

For example, it will be understood by those skilled in the art that software used by the vaginal device may be located in any location in which it may be accessed by the system. It will be further understood by those of skill in the art that the number of variations of the network, location of the software, and the like are virtually limitless. It is intended, therefore, that the subject matter in the above description shall be interpreted as illustrative and shall not be interpreted in a limiting sense.

For example, embodiments of the invention could operate on a wide range of mobile devices other than mobile phones, tablets, and computers without substantially affecting the functioning of embodiments of the invention.

While the above representative embodiments have been described with certain components in exemplary configurations, it will be understood by one of ordinary skill in the art that other representative embodiments can be implemented using different configurations and/or different components.

For example, it will be understood by one of ordinary skill in the art that the order of certain steps and certain components can be altered without substantially impairing the functioning of the invention.

The representative embodiments and disclosed subject matter, which have been described in detail herein, have been presented by way of example and illustration and not by way of limitation. It will be understood by those skilled in the art that various changes may be made in the form and details of the described embodiments resulting in equivalent embodiments that remain within the scope of the invention. It is intended, therefore, that the subject matter in the above description shall be interpreted as illustrative and shall not be interpreted in a limiting sense.

What is claimed is:

1. A vaginal device configured to be inserted in a vagina of a user, the vaginal device comprising:
    a body comprising at least two electrodes configured to measure a fertility-related parameter of the user;
    a power source configured to provide power to the device; and an electrical system operably connected to the power source, the electrical system operably connected to one or more of the electrodes, the electrical system comprising two P-channel metal oxide semiconductor field effect transistors (MOSFETs) that the system holds in a high impedance state, the electrical system further comprising a plurality of N-channel MOSFETs, the high impedance of the P-channel MOSFETS causing the N-channel MOSFETS to also be held in a high impedance state, the electrical system configured to switch one or more of the electrodes between charging and measuring functions.

2. The vaginal device of claim 1, wherein the body comprises the power source.

3. The vaginal device of claim 1, wherein the body comprises the electrical system.

4. The vaginal device of claim 1, wherein the fertility-related parameter comprises one or more of electrical impedance, basal body temperature, vaginal pH, heart rate, and another fertility-related parameter relating to the user's vaginal mucus.

5. The vaginal device of claim 1, wherein the device further comprises a communication system configured to transmit one or more of a fertility-related parameter and other data generated by the device to an external database.

6. The vaginal device of claim 5, wherein the communication system is further configured to receive data from the external database.

7. The vaginal device of claim 5, wherein the communication system is wireless.

8. The vaginal device of claim 5, wherein the external database is configured to do one or more of store and analyze fertility-related parameters.

9. The vaginal device of claim 1, further comprising a tail, the tail physically connected to the body.

10. The vaginal device of claim 9, wherein the body is configured to be inserted into the vagina.

11. The vaginal device of claim 10, wherein the tail is configured to protrude from the vagina while the body is inserted into the vagina, wherein the tail is further configured to be holdable by the user so as to remove the vaginal device from the vagina.

12. The vaginal device of claim 9, wherein the tail is configured to serve as an antenna for wireless communication.

13. The vaginal device of claim 1, wherein the power source comprises a battery.

14. The vaginal device of claim 13, wherein the battery comprises a lithium ion battery.

15. The vaginal device of claim 1, wherein one or more of the body and the electrodes are made of a biocompatible material.

16. The vaginal device of claim 1, wherein the electrical system comprises at least one low-pass filter capacitor.

17. The vaginal device of claim 1, wherein the low-pass filter capacitor increases a sensitivity of a measurement of the electrical impedance of the user's vaginal mucus.

18. The vaginal device of claim 1, wherein the electrical system comprises at least one diode.

19. The vaginal device of claim 18, wherein the diode permits ESD protection without significantly affecting measurement of fertility-related parameters.

20. The vaginal device of claim 1, wherein the electrodes are configured to measure the fertility-related parameter by contacting fluids of the vagina.

21. The vaginal device of claim 1, wherein the body is squeezable by the user.

22. The vaginal device of claim 1, wherein one or more of the body and one or more of the electrodes are one or more of resistant to humidity and substantially humidity-proof.

23. The vaginal device of claim 1, wherein one or more of the body and the electrodes are one or more one or more of water-resistant and substantially waterproof.

24. The vaginal device of claim 1, further comprising a charging cradle configured to do one or more of protect the vaginal device and hold the vaginal device in place for charging of the power source.

25. The vaginal device of claim 24, wherein the charging cradle comprises a charging interface configured to electrically connect with and charge at least one of the electrodes.

26. The vaginal device of claim 25, wherein the charging interface comprises a spring loaded charging node.

27. The vaginal device of claim 25, wherein the charging interface comprises a pin.

28. The system of claim 1, wherein the high impedance state in which the system holds the two P-channel MOSFETs causes a plurality of N-channel MOSFETS to be pulled to a zero voltage.

29. The system of claim 1, wherein the electrical system provides a current across the electrodes, charging the electrodes without causing interference.

30. The system of claim 29, wherein voltage across the electrodes relates to electrical impedance of the user's vaginal mucus to directly measure this impedance.

31. A method for measuring a fertility-related parameter of a user, comprising:
  measuring, by a vaginal device configured to be inserted in a vagina of the user, a fertility-related parameter of the user, the vaginal device comprising: a body comprising at least two electrodes configured to measure a fertility-related parameter of the user; a power source configured to provide power to the device; and an electrical system operably connected to the power source, the electrical system operably connected to one or more of the electrodes, the electrical system comprising two P-channel metal oxide semiconductor field effect transistors (MOSFETs) that the system holds in a high impedance state, the electrical system further comprising a plurality of N-channel MOSFETs, the high impedance of the P-channel MOSFETS causing the N-channel MOSFETS to also be held in a high impedance state, the electrical system configured to switch one or more of the electrodes between charging and measuring functions;
  relaying, by the vaginal device, the fertility-related parameter to an external database system;
  receiving, by the vaginal device, from the external database system analysis of the fertility-related parameter by the external database system; and
  providing, by the vaginal device, to the user, using the system analysis, fertility information regarding the user.

32. The method of claim 31, wherein the fertility information comprises feedback to the user generated using one or more of the fertility-related parameters and the system analysis.

33. The method of claim 32, wherein the feedback comprises information regarding one or more of natural conception and natural contraception.

34. The method of claim 33, wherein the system analysis comprises a timing estimate obtained using an algorithm configured to estimate a timing of an ovulation cycle of the user, the estimate based on a graph of impedance of vaginal mucus relative to a day of ovulation cycle.

35. The method of claim 33, wherein one or more of the steps in the method is performed using a software system running on a user-operated mobile device.

36. The system of claim 30, wherein the system controls voltage across the electrodes, the system further preventing substantial interference while the electrodes measure the electrical impedance of the user's vaginal mucus while charging.

* * * * *